United States Patent
Nichols et al.

(10) Patent No.: US 6,961,448 B2
(45) Date of Patent: Nov. 1, 2005

(54) USER AUTHENTICATION IN MEDICAL DEVICE SYSTEMS

(75) Inventors: Timothy J. Nichols, Lino Lakes, MN (US); David L. Thompson, Andover, MN (US)

(73) Assignee: Medtronic, Inc., Minneapolis, MN (US)

( * ) Notice: Subject to any disclaimer, the term of this patent is extended or adjusted under 35 U.S.C. 154(b) by 713 days.

(21) Appl. No.: 09/750,739

(22) Filed: Dec. 29, 2000

(65) Prior Publication Data

US 2001/0031071 A1 Oct. 18, 2001

Related U.S. Application Data

(60) Provisional application No. 60/173,822, filed on Dec. 30, 1999.

(51) Int. Cl.[7] .............................................. G06K 9/00
(52) U.S. Cl. ......................... 382/115; 607/31; 340/5.8
(58) Field of Search ....................... 382/115, 116, 128; 607/30, 31, 32; 340/5.82, 5.83, 5.84, 5.85, 340/5.52, 5.53, 5.54, 5.8, 5.81

(56) References Cited

U.S. PATENT DOCUMENTS

| | | | | |
|---|---|---|---|---|
| 4,993,068 | A | * | 2/1991 | Piosenka et al. ............. 713/186 |
| 5,345,362 | A | | 9/1994 | Winkler ....................... 361/681 |
| 5,401,561 | A | | 3/1995 | Fisun et al. .................. 428/195 |
| 5,456,692 | A | | 10/1995 | Smith, Jr. et al. .............. 607/31 |
| 5,626,621 | A | | 5/1997 | Skoglund et al. .............. 607/10 |
| 5,787,185 | A | * | 7/1998 | Clayden ....................... 382/115 |
| 5,838,306 | A | | 11/1998 | O'Connor et al. ........... 345/163 |
| 6,132,363 | A | * | 10/2000 | Freed et al. ................... 600/16 |
| 6,615,191 | B1 | * | 9/2003 | Seeley ........................ 705/54 |

FOREIGN PATENT DOCUMENTS

| | | | | |
|---|---|---|---|---|
| WO | 0021021 | 4/2000 | ............ G06K 9/00 |
| WO | 0022581 | 4/2000 | ............ G07C 9/00 |
| WO | 0026823 | 5/2000 | ............ G06F 17/30 |
| WO | 0043960 | 7/2000 | ............ G07C 9/00 |

* cited by examiner

Primary Examiner—Yon J. Couso
(74) Attorney, Agent, or Firm—Girma Wolde-Michael; Michael C. Soldner (57) ABSTRACT

A user authentication system utilizes biometric traits such as fingerprints, vein print, voice print, facial images, iris/retina and similar distinguishing characteristics to allow access to programmers, ETPs, PSAs and similar instruments associated with implantable medical devices (IMDs). The authentication system provides a hierarchical scheme that allows access based on expertise and need basis.

15 Claims, 5 Drawing Sheets

USER AUTHENTICATION IN MEDICAL DEVICE SYSTEMS

CROSS-REFERENCE TO RELATED APPLICATIONS

This application claims the benefit of U.S. Provisional Application No. 60/173,822, filed Dec. 30, 1999, "User Authentication in Medical Device Systems." The disclosure and drawings of the provisional application are specifically incorporated herein by reference.

FIELD OF THE INVENTION

The present invention generally relates to medical device systems. Specifically, the invention relates to biometric-based identification systems to provide a hierarchy of authorized access to operational hardware and software tools in medical devices. The biometric data may represent iris/retina, fingerprint, voiceprint, facial, veinal and similar biometric identification traits of individuals. These are stored in a database to confirm identification of an authorized person based on a correspondingly comparative code assigned to the biometric traits of a specific user. The identification code may be implemented in instruments such as a programmer, pacing system analyzer (PSA), external temporary pacemaker (ETP), home monitor and other peripheral units that are in data communication with implanted devices in a patient. Access to specific therapy and diagnostic tools and content are based on the hierarchy of authorization such as, for example, a doctor, a nurse, a patient, or a Medtronic employee, each of which would have qualified access granted with respect to their expertise and need basis.

BACKGROUND OF THE INVENTION

The present invention is compatible and complementary with the elements disclosed in the following pending applications: "Medical System Having Improved Telemetry," filed Jul. 19, 1999, Ser. No. 09/356,340; "System and Method for Transferring Information Relating to an Implantable Medical Device to a Remote Location," filed on Jul. 21, 1999, Ser. No. 09/358,081; "Apparatus and Method for Remote Troubleshooting, Maintenance and Upgrade of Implantable Device Systems," filed on Oct. 26, 1999, Ser. No. 09/426,741; "Tactile Feedback for Indicating Validity of Communication Link with an Implantable Medical Device," filed Oct. 29, 1999, Ser. No. 09/430,708; "Apparatus and Method for Automated Invoicing of Medical Device Systems," filed Oct. 29, 1999, Ser. No. 09/429; "Apparatus and Method for Remote Self-Identification of Components in Medical Device Systems," filed Oct. 29, 1999, Ser. No. 09/429,956; "Apparatus and Method to Automate Remote Software Updates of Medical Device Systems," filed Oct. 29, 1999, Ser. No. 09/429,960; "Method and Apparatus to Secure Data Transfer From Medical Device Systems," filed Nov. 2, 1999, Ser. No 09/431,881 "Implantable Medical Device Programming Apparatus Having An Auxiliary Component Storage Compartment," filed Nov. 4, 1999, Ser. No. 09/433,477; "Remote Delivery Of Software-Based Training For Implantable Medical Device Systems," filed Nov. 10, 1999, Ser. No. 09/437,615; "Apparatus and Method for Remote Therapy and Diagnosis in Medical Devices Via Interface Systems," filed Dec. 14, 1999, Ser. No. 09/460, 580; "Virtual Remote Monitor, Alert, Diagnostics and Programming For Implantable Medical Device Systems" filed Dec. 17, 1999, Ser. No. 09/466,284; "Instrumentation and Software for Remote Monitoring and Programming of Implantable Medical Devices (IMDs), filed Dec. 2, 1999, Ser. No. 60/172,937; "Application Proxy For Telecommunication-enabled Remote Medical Access Instruments," filed Dec. 23, 1999, Ser. No. 60/173,081; "Information Network Scheme For Interrogation Of Implantable Medical Devices (IMDs)," filed Dec. 24, 1999, Ser. No. 60/173,064; "Medical Device GUI For Cardiac Electrophysiology Display And Data Communications," filed Dec. 24, 1999, Ser. No. 60/173,065; "Integrated Software System For Implantable Medical Device Installation And Management," filed Dec. 24, 1999, Ser. No. 60/173,082; "Dynamic Bandwidth Monitor And Adjuster For Remote Communications With A Medical Device," filed Dec. 24, 1999, Ser. No. 60/173,083 "Large-Scale Processing Loop For Implantable Medical Devices (IMDs)," filed Dec. 24, 1999, Ser. No. 60/173,079; "Chronic Real-Time Information Management Systems For Implantable Medical Devices (iIVIDs)," filed Dec. 24, 1999, Ser. No. 60/173,062; "Automatic Voice and Data Recognition For Medical Device Instrument Systems," filed Dec. 24, 1999, Ser. No. 60/173,071 "Central Switchboard to Facilitate Remote Collaboration With Medical Instruments," filed Dec. 24, 1999, Ser. No. 60/173,080; "System Of Notification Of Recalled Components For A Medical Device" filed Dec. 29, 1999, Ser. No. 09/474,694; "A Communications System For An Implantable Device And A Drug Dispenser" Dec. 30, 1999, Ser. No. 09/475,709; "User Authentication In Medical Systems Device," filed Dec. 30, 1999, Ser. No. 60/173,822; "Automated Invoicing Based On Medical System Usage," filed Dec. 30, 1999, Ser. No 60/173,824; which are all incorporated by reference herein in their entireties.

Medical devices, particularly implanted medical devices, require occasional and at times, chronic adjustments based on therapy and diagnostic needs of the patient. The therapy and diagnostic parameters that need adjustments may involve the decisions of doctors, nurses, Medtronic field service personnel, patients, members of the patient's family or representative, as the case may be. Further, the parameters to be adjusted, or the software to be implemented, in a medical device via an instrument such as a programmer or instruments, would require various levels and hierarchies of expertise. Misadjustment of the parameters could endanger the patient's life. Accordingly, there is need to limit access to these instruments to primarily protect the patient's privacy and well being.

Therapy regimen, and chronic patient and care treatment, via implanted medical devices would require timely decisions by physicians qualified to assess the patient's conditions and dispense proper medical care. Further, implanted medical devices (IMDs) must be monitored on a regular or chronic basis to make adjustments of certain parameters or settings responsive to changes in a patient's condition or based on factors internal to the IMD. IMDs may also contain logic devices such as digital controllers which may need to undergo firmware or software upgrades or modifications. Further, various users, including doctors, nurses, Medtronic field personnel and the patient, may occasionally want to review physiologic data or patient information stored in IMDs to evaluate the performance of the device and review patient history as needed. Current practice provides operations in which software and instructions installed in an IMD could be modified responsive to patient diagnostic and therapeutic conditions.

Instruments such as programmers, PSAs, ETPs and similar devices are becoming ubiquitous. Specifically, as the segment of the population with IMDs increases, health care cost management would require various home monitors and instruments to be available at the disposal of patients for managing the operations of the IMDs, either by the patients, nurses or doctors, as the case may be. For example, the patient may be remotely instructed to adjust certain parameters without intervention of the physician. Similarly, in the case of a chronic patient, a nurse may be assigned to visit the individual at home so that the nurse may make qualified decisions to adjust or modify the operations of the IMD based on a review of diagnostic and therapeutic parameters retrieved from the device. While empowering patients and other qualified personnel is a viable economic option to reduce the cost of health care, user verification, user authorization and access control will clearly be needed to provide a secure and safe management of implanted devices in patients. Specifically, all peripheral and major devices that are used in downlinking to the IMD may potentially be a source of security and privacy breach unless protected by a security system.

There are several user authentication systems. Specifically, some implement biometric identification to control access to customize computer systems data. For example, some computers require fingerprint data to access users' sensitive information.

In this regard, PCT publication WO2000/22581 to Bromba, M., discloses an identification device with a sensor having an authentication surface with biometric features. A comparator compares detected biometric features of a part of the authentication surface of an authorized person or persons to determine the relative position of the sensor detected biometric features within the authentication surface. The computing device then computes an identification code which identifies the person detected by the sensor.

Similarly, U.S. Pat. No. 5,401,561 to Borus et al, discloses identification characteristics formed as optical markings with radiation provided by a light source. The marking is in an optically transparent housing or surface or other area for at least a part of the wavelength range within the sensitivity range of the human eye and for a further part outside the human eye sensitivity range.

PCT publication WO2000/43960 to Frischholz, R., discloses a recognition system that is based upon medical data, obtained for example, from fingerprints or eyes. The method involves acquisition of data by scanning with a camera, for comparison with reference data. In order to prevent misuse, the reference data is based upon several samples from different positions. The user has to move a hand or eyes to form an object on the screen that would provide adequate data input to the controller. Similarly, PCT publication WO2000/021021 to Frischholz, R., discloses a face detecting system in which the images of a face model could be generated for identification purposes.

PCT publication WO2000/026823 to Garfinkle, N., discloses an individual medical record protection method for protecting medical records prepared in a doctors office or hospital. Specifically, the invention relates to a process by which a person authorized by the patient inputs personal identification and biometric codes to a database that checks if the biometric and Id number are in accord with that stored in the database. Upon confirmation, access is granted to a particular record that uses the Id code and the data is transmitted to the requesting site.

Accordingly, the use of biometrics for identification and authorization of users based on data associated with a stored key is well known in the art. However, the implementation of biometric recognition systems to enable access to instruments in data communication with IMDs, presents new and non-obvious biometric implementation. Specifically, the implementation of biometric recognition systems to provide a layered and hierarchal access to instruments and IMDs on expertise and need, reduces opportunities for tampering, manipulation, error and harm to the patient. Accordingly, it is preferable to provide specific access to IMDs via instruments such as programmers, PSAs and other instruments, home monitors and programmers to doctors, nurses, Medtronic technicians and patients or patients' representatives, to enable safe monitoring and content specific adjustment or modifications of implanted medical devices.

SUMMARY OF THE INVENTION

The present invention provides a system for selective implementation of biometric user and instrument identification that enables secure and accurate data transfer between IMDs and instruments such as programmers. Embodiments of suitable biometric user authentication systems include, for example, user identification and password schemes, a scan of written signatures, biometric identification based on retina/iris or other unique body features, voice recognition, fingerprints, vein prints and similar biometric recognition traits hereinafter referred to as "biometric traits".

BRIEF DESCRIPTION OF THE DRAWINGS

FIG. 2 is a perspective view of an external programming unit. The invention utilizes the biometric traits to insure the identity of users. Further, the system enables segregated access to certain tools, text and operations based on the user's expertise, need and qualifications. For example, physicians have a broad-based access to therapeutic and diagnostic tools compared to nurses, technicians or the patients.

DETAILED DESCRIPTION OF THE DRAWINGS

Figure 1:
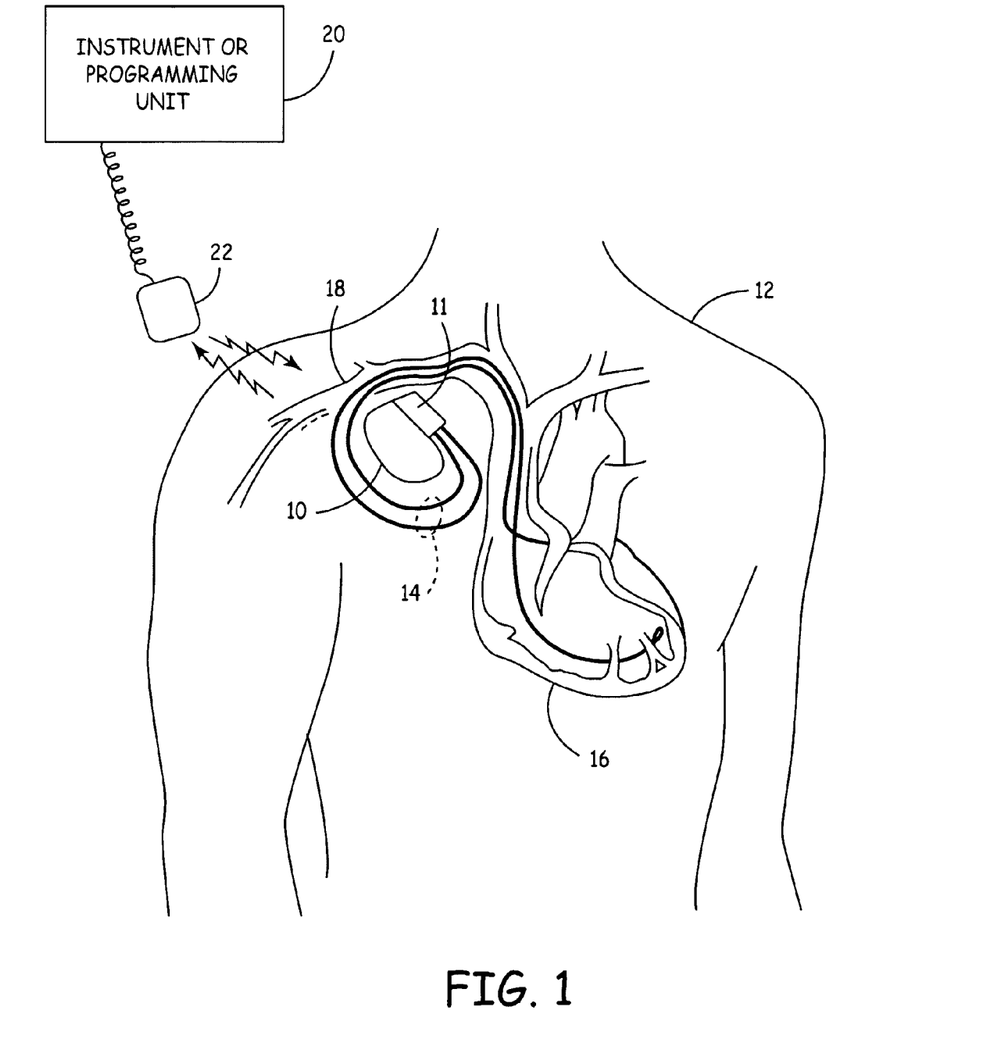
FIG. 1 is an illustration of a body implanted device system in accordance with the present invention, including an instrument such as a programmer in wireless data communication with the implanted medical device.

FIG. 1 is an illustration of an implantable medical device (IMD) system adapted for use in accordance with the present invention. The medical device system of FIG. 1 includes an IMD 10 implanted in patient 12. In accordance with conventional practice in the art, IMD 10 is housed within a hermetically sealed, biologically inert outer casing which may be conductive, to serve as an indifferent electrode in the IMD's pacing/sensing circuit. One or more pacemaker leads collectively identified with reference numeral 14 in FIG. 1 are electrically coupled to IMD 10 in a conventional manner and extend into the patient's heart 16 via vein 18. Disposed generally near the distal end of leads 14, are one or more exposed conductive electrodes for receiving electrical cardiac signals and/or for delivering electrical pacing stimuli to heart 16. As will be appreciated by those of ordinary skill in the art, leads 14 may be implanted with each distal end situated in the atrium and/or ventricle of heart 16. Although the present invention will be described herein referring to this one embodiment which includes IMD 10, those of ordinary skill in the art, in light of the present disclosure, will appreciate that the present invention may be alternately practiced in connection with numerous other types of IMDs.

Further referring to FIG. 1, an instrument/external programming unit 20 is shown in wireless data communication with IMD 10. Instrument 20 includes a programming head 22 in accordance with conventional medical device programming systems for facilitating two way communication between IMD 10 and instrument 20. In many known implantable device systems, a programming head such as that depicted in FIG. 1 is positioned on the patient's body over the implant side of the device such that one or more antennae within head 22 can send RF signals to, and receive RF signals from, an antenna disposed within the hermetic enclosure of IMD 10 or disposed within the connector block of IMD 10 in accordance with common practice in the art.

Figure 2:
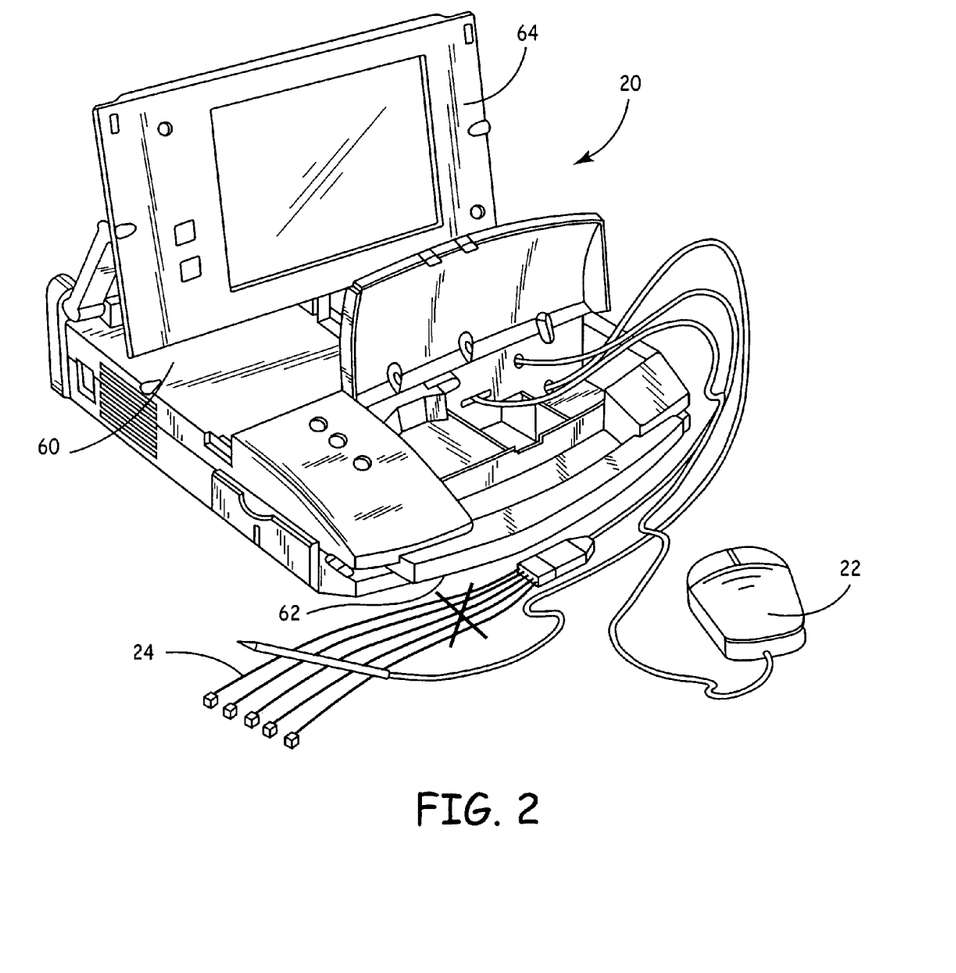

FIG. 2 is a perspective view of instrument or programming unit 20 in accordance with the present invention. Generally, programmer 20 includes a processing unit (not shown in the figure) that, in accordance with the presently disclosed invention, is a personal computer type mother board, for example, computer motherboard including an Intel PentiumIII microprocessor and related circuitry such as digital memory. The details of design and operation of the programmer's computer system will not be set forth in detail in the present disclosure, as it is believed that such details are well known to those of ordinary skill in the art.

Further, referring to FIG. 2, programmer 20 comprises an outer housing 60 which is preferably made of a thermal plastic or equivalent rugged yet relatively lightweight material, and a carrying handle 62 integrally formed into the front of housing 60. Handle 62 is retractably designed to serve as a handle so that programmer 20 can be carried like a briefcase. An articulating display screen 64 is disposed on the upper surface of housing 60. Display screen 64 folds down into a closed position (not shown) when programmer 20 is not in use, thereby reducing the size of programmer 20 and protecting the display surface of display 64 during transportation and storage thereof.

As would be appreciated by those of ordinary skill in the art, it is often desirable to provide a means for determining the status of the patient's conduction system. This is generally accomplished by external ECG leads 24 which can provide suitable ECG tracings. Further, in accordance with the present invention, programmer 20 is equipped with an internal printer (not shown) so that a hard copy of a patient's ECG or graphics could be generated at display screen 64. Several types of printers such as AR 100 Printer from General Scanning Company are compatible with programmer 20.

Still referring to FIG. 2, programmer 20 is shown with articulating display screen 64, having been lifted up into one of a plurality of possible open positions so that the display area thereof is visible to users situated in front of programmer 20. Articulating display screen is preferably of the LCD or electro luminous type characterized by being relatively thin, as compared, for example a CRT or the like. As would be appreciated by those with ordinary skill in the art, display screen 64 is operatively coupled to the computer circuitry, disposed within housing 60, and is adapted to provide a visible display of graphics and/or data under control of the internal computer.

Programmer 20 as illustrated herein with reference to FIG. 2 is substantially disclosed and described in more detail in U.S. Pat. No. 5,345,362 to Thomas J. Winkler, entitled "Portable Computer Apparatus with Articulating Display Panel", which patent is incorporated herein by reference in its entirety. The Medtronic Model 9790 Programmer is the implantable device programming unit with which the present invention may be advantageously practiced.

Figure 3:
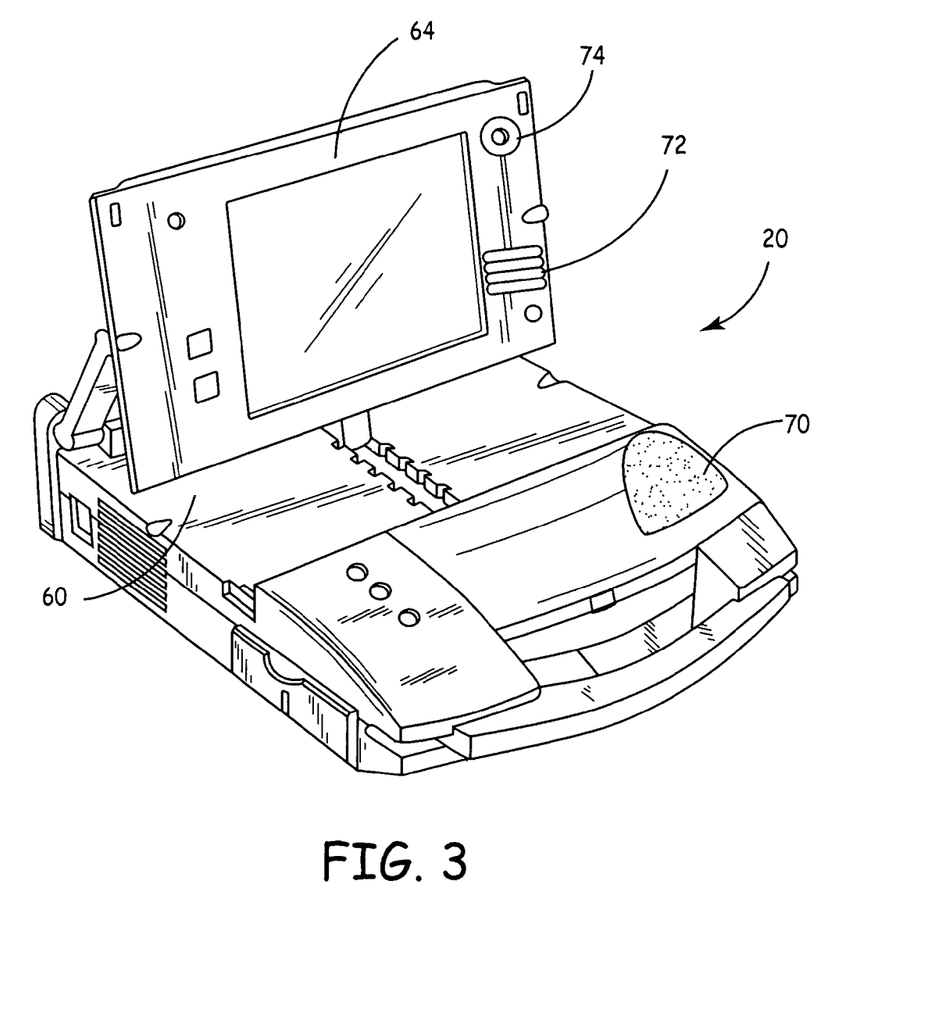
FIG. 3 is a perspective view of an external programming unit with biometric recognition systems implemented therein.

FIG. 3 is a perspective view of programming unit 20 incorporating the biometric identification systems in accordance with the present invention. Specifically, biometric sensor 70 for detecting fingerprints includes an area adapted to fit the front part of a user's finger. Similarly, microphone 72 is implemented on panel 64 to enable voice recognition. Further, camera 74 is implemented to enable reading of facial and other bodily features including iris/retina scans.

Figure 4:
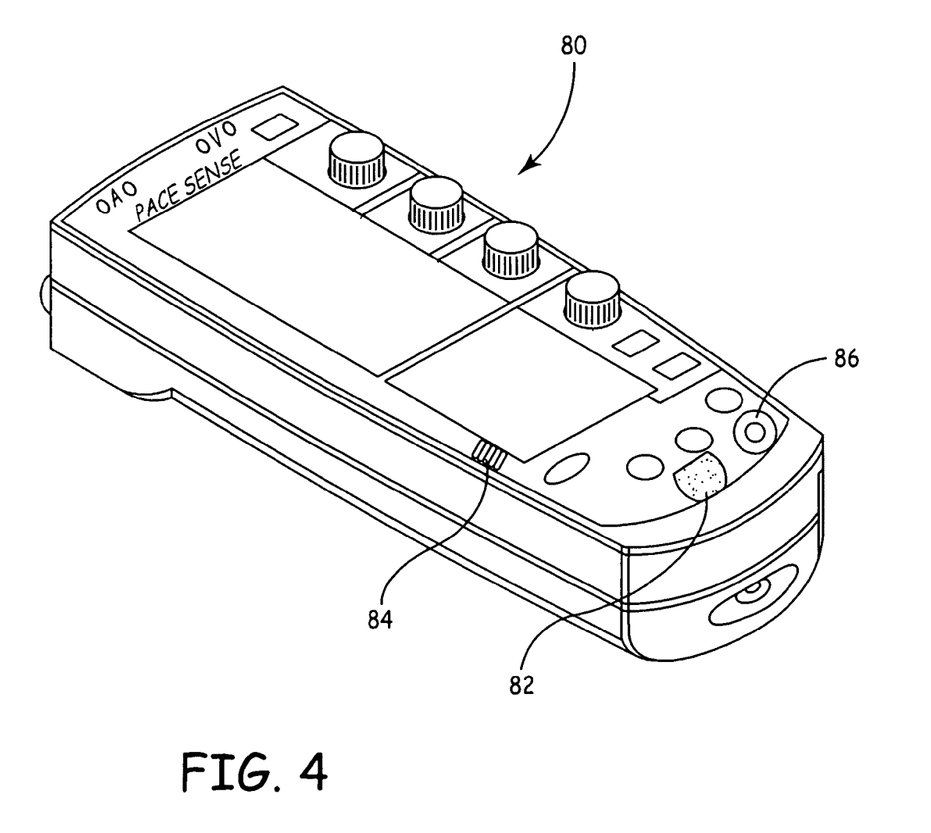
FIG. 4 is a perspective view of an external programming unit, such as an ETP, the biometric recognition system implemented therein.

FIG. 4 is a perspective view of ETP 80. Generally, ETP 80 is a mode switching apparatus for an external dual chamber cardiac pacemaker having multiple single chamber and dual chamber primary pacing modes and user adjustable atrial and ventricular sensitivities. The dual chamber demand pacing mode, for example, the DDE or DDI mode, is in effect as long as the atrial and ventricular pace pulse amplitudes are set by the user within an operative range. The pacing mode is switched to a single chamber demand mode when one of the atrial and ventricular pace pulse energies is set to an inoperative setting, which preferably is a no output setting. If the atrial pace pulse amplitude is set to no output, then the mode is switched to a single chamber demand mode with ventricular sensing and pacing, preferably the VVI mode. If the ventricular pace pulse amplitude is set to no output, then the mode is switched to a single chamber mode with atrial sensing and pacing, preferably the AAI mode. In the implementation of ETP 80, the setting of atrial or ventricular pace pulse amplitude to the off position is detected and the corresponding atrial or ventricular sense amplifier is effectively rendered inoperative resulting in the mode switch. The mode switch back to the dual chamber demand pacing mode is affected by setting the atrial or ventricular pace pulse amplitude to any level other than the no output position. Preferably, the mode switch is to the DDD mode, even if the preceding mode switch was from the DDI mode.

ETP 80 described herein with reference to FIG. 4 is substantially disclosed in more detail in U.S. Pat. No. 5,626,621 to Skoglund et al, entitled "Dual Chamber Multi-Mode External Pacemaker", which patent is incorporated herein by reference in its entirety. ETP 80 includes sensor 82 for detecting fingerprints, sensor 86, which includes a camera, to sense biometric data representing images and/or the iris and microphone 84 for collecting biometric data representing voiceprint and voice recognition systems.

Figure 5:
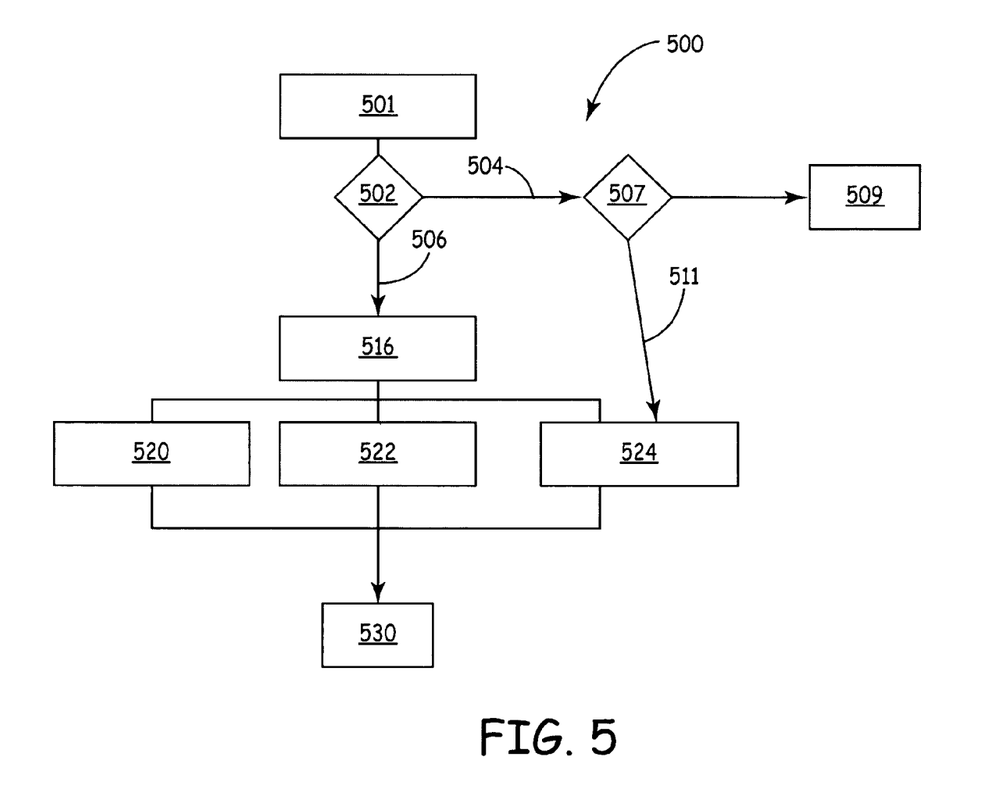
FIG. 5 is a flow chart of one embodiment of the user authentication process in accordance with the present invention.

FIG. 5 is a flow chart of one embodiment of the user identification and authorization process 500 in accordance with the present invention. Specifically, when a user attempts to gain access to IMD 10, programmer 20 or ETP 80, the user enters appropriate authentication data at step 501. The identification data may include a fingerprint, an image, iris scan, voiceprint, or similar biometric traits. The system analyzes the input by preferably comparing it with stored data. If a match is confirmed, access is granted based on the authorization level to access specific tools and features of programmer 20, IMD 10 or ETP 80, as the case may be. Specifically, if authorization is confirmed, and access is authorized as shown at logic step 506, then step 516 determines the type of access and level under the authorization scheme for the specific user based on content, class or category assigned to the user as appropriate. For example, step 520 illustrates a third user or an untrained user who may have only limited usage/access rights such as no access to programmable operations or patient data. Step 522, however, may permit broader access such as perhaps are afforded to a doctor. Further, a nurse of appropriate identification may be granted access to limited programmable operations relating to diagnostic and therapy tools. Similarly, a patient user may be authenticated to access a limited set of tools that may be permitted to adjust non-critical settings. Furthermore, a Medtronic field representative may be allowed to access only operational/functional aspects that relate to data collection and/or software upgrades, with strict limitations to any or all therapy and diagnostic tool adjustments. Alternatively, step 524 might be identified with the user's authentication and authorization category, and it may equate to that of a trained specialist. For example, this authorization may relate to someone who is authorized for access to programmable operations, patient data or other rights. Step 530 designates an end to the authorization sequence of a session. Logic pathway 504 represents the denial of user access. However, in this scenario, step 507 queries whether the user is requesting access in view of a special override function or emergency situation. If not, then the authentication is denied at step 509. In the event the special override function is approved, then logic pathway 511 routes the user to step 524. As indicated hereinabove, step 524 is normally identified with the user's identification and authorization category relating to a trained specialist and may provide a broad-based access to diagnostic, therapeutic and operational/functional features of programmer 20, IMD 10 and ETP 80.

It should be recognized that FIG. 5 is merely one embodiment of a number of authentication schemes and logic systems enabled and claimed by this invention disclosure. Indeed, authentication system 500 may include combinations of hardware and software elements suitable for interface with the various instruments such as programmers, ETPs, PSAs and home monitors, to provide authorized access to these devices using the biometric identification system disclosed herein.

As indicated hereinabove, biometric data or traits used to authenticate and verify users may include retina or iris scans, fingerprint scans, vein print scans, voice prints, or voice recognition system, special geometry/facial recognition, hand geometry, veinal scans, and similar other biometric traits and features that could be used to positively identify a user. The authentication techniques implemented in the present invention include hierarchical schemes of grant to primary, secondary and occasional users. For example, doctors and nurses could be considered primary users, having access to specific therapeutic and diagnostic tools, both instruments and IMDs.

In addition to the various biometric techniques disclosed in the present invention, instrument and IMD related authentication mechanisms may include verification through use of; inscription techniques, approved serial numbers, fixed or pre-loaded data signatures in the instrument or IMD memory, resistance or other electrical or digital characteristic matching, load recognition, or data message generated by one or more predetermined algorithm based on dates, events, serial number or other phenomenon.

Referring now to FIGS. 3 and 4, the implementation of the various biometric identification systems in programmer 20 and ETP 80, include voice recognition via microphone 72 and 84 respectively, face recognition or iris scan using camera 74 or 86 respectively, and fingerprint recognition using fingerprint sensors 70 and 82 respectively. The iris scan and face recognition biometric systems may be the type manufactured by Iris Scan, Inc., Symtron Technology, Dialog Communication Systems, Visionics Corp. Further, biometric fingerprint sensors may be of the type supplied by Miaxis Biometrics Co., Advanced Biometric Solutions, Veridicon Face Sense, and Precise Biometrics. Further, voice recognition systems for voice print identification may be of the type offered by Dialogue Communication Systems.

Accordingly, the biometric identification systems contemplated by the present invention may be implemented from various suppliers for incorporation in programmer 20, ETP 80 and similar instruments. One of the significant aspects of the present invention includes the implementation of biometric data to eliminate error, tampering and provide patients with a high level of security to maintain medical data privacy.

Although the invention is described with reference to particular embodiments, it will be understood to those skilled in the art that this embodiment is merely illustrative of the application of the principles of the invention. Numerous modifications may be made therein, and other arrangements may be devised without departing from the spirit and scope of the invention.

What is claimed is:

1. A user recognition system to identify a user and enable access to instruments associated with at least one implanted medical device, the system comprising:
   an implanted medical device in a patient;
   an instrument in data communications with the implanted medical device;
   a memory associated with the implanted medical device storing coded data representative of biometric traits of authorized users to be granted access to the data communications of the instrument;
   a sensor unit positioned along the instrument for generating biometric traits of the user; and
   an analyzer unit determining whether a potential user is authorized to have access to the data communications of the instrument, wherein, in response to the potential user not being authorized to have access, the analyzer unit determines whether the potential user is requesting access associated with an override function and, in response to the access request being associated with the overdrive function, granting a level of access associated with a predetermined authorization level.

2. The system of claim 1 wherein said implanted medical device includes one of a pacer, a defibrillator, a drug delivery device and a neural implant.

3. The system of claim 1 wherein said instrument includes one of a programmer, a PSA and a home monitor.

4. The system of claim 1 wherein said sensing unit includes at least one of a finger scanner, a camera and a microphone.

5. The system of claim 4 wherein said biometric traits include a finger scan obtained from said finger scanner.

6. The system of claim 4 wherein said biometric traits include one of an iris scan and a retina scan obtained via said camera.

7. The system of claim 4 wherein said biometric traits include a voice print obtained from said microphone.

8. A biometric-based user authentication system for identifying and granting access to at least one user to an implanted medical device in a patient associated with an instrument, the authentication system comprising:
   at least one biometric sensor implemented in the instrument;
   at least one biometric trait of a user stored as coded data in a memory bank of said biometric sensor; and
   means for analyzing and comparing said at least one biometric trait with said coded data to grant or deny access, wherein, in response to a potential user being denied access, the analyzing means determines whether the potential user is requesting access associated with an override function and, in response to the access request being associated with the overdrive function, granting a level of access associated with a predetermined authorization level.

9. The system of claim 8 wherein said at least one biometric sensor includes at least one of a camera, a finger print sensor and a microphone.

10. The system of claim 8 wherein said at least one biometric trait of a user includes, a fingerprint a voice print, an iris print, a retinal print, a facial model, a veinal imprint and a digital signature.

11. The system of claim 8 wherein said means for analyzing and comparing includes a software system implemented in the memory bank of the biometric sensor.

12. The system of claim 8 wherein said biometric traits of a user stored as coded data includes instructions to allow a user with matching biometric traits to have access to a pre-determined set of data and tools of said implanted medical device.

13. A method for a biometric-based identification of a user to provide authorized access to operational hardware, software and patient medical data contained in instruments and implanted medical devices, the method comprising:

accepting at least one biometric trait from a potential user;

comparing said at least one biometric trait to a stored coded data;

granting a qualified access when a match is confirmed between said at least one biometric trait and the stored coded data; and determining, in response to a match not being confirmed between said at least one biometric trait and the stored coded data, whether the potential user is requesting access associated with an override function and, in response to the access request being associated with the overdrive function, granting a level of access associated with a predetermined authorization level.

14. The method of claim 13 wherein said qualified access includes a hierarchical scheme to enable user-specific access and authorization based on expertise and need.

15. The method of claim 14 wherein said hierarchical scheme includes distinctions of access to various hardware, software tools to perform therapy, diagnostic and monitoring functions designed to provide various levels of authorized access to physicians, nurses, Medtronic technicians, patients and their representatives.

* * * * *

UNITED STATES PATENT AND TRADEMARK OFFICE
CERTIFICATE OF CORRECTION

PATENT NO. : 6,961,448 B2  
APPLICATION NO. : 09/750739  
DATED : November 1, 2005  
INVENTOR(S) : Timothy J. Nichols et al.

It is certified that error appears in the above-identified patent and that said Letters Patent is hereby corrected as shown below:

Claim 10, Col. 9, line 5, delete "a fingerprint a voice print,"

and insert in place there of -- a fingerprint, a voice print, --.

Signed and Sealed this

Twenty-fourth Day of February, 2009

JOHN DOLL  
*Acting Director of the United States Patent and Trademark Office*